(12) United States Patent
Irisawa

(10) Patent No.: US 8,473,037 B2
(45) Date of Patent: Jun. 25, 2013

(54) OPTICAL CABLE AND OPTICAL COHERENCE IMAGING DIAGNOSTIC APPARATUS USING THIS CABLE

(75) Inventor: Yuichiro Irisawa, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 457 days.

(21) Appl. No.: 12/649,060

(22) Filed: Dec. 29, 2009

(65) Prior Publication Data

US 2010/0130872 A1 May 27, 2010

Related U.S. Application Data

(63) Continuation of application No. PCT/JP2008/061487, filed on Jun. 24, 2008.

(30) Foreign Application Priority Data

Jun. 29, 2007 (JP) ................................. 2007-172932

(51) Int. Cl.
*A61B 6/00* (2006.01)
(52) U.S. Cl.
USPC ........... 600/478; 600/407; 600/476; 600/477; 606/1
(58) Field of Classification Search
USPC ........................ 600/476, 477, 478; 606/1–19
See application file for complete search history.

(56) References Cited

U.S. PATENT DOCUMENTS

| | | | |
|---|---|---|---|
| 6,456,768 B1 | 9/2002 | Boncek et al. | |
| 7,952,718 B2* | 5/2011 | Li et al. | 356/479 |
| 2005/0201662 A1* | 9/2005 | Petersen et al. | 385/12 |
| 2007/0233396 A1* | 10/2007 | Tearney et al. | 702/19 |

(Continued)

FOREIGN PATENT DOCUMENTS

| | | |
|---|---|---|
| JP | 7-306342 A | 11/1995 |
| JP | 8-262287 A | 10/1996 |

(Continued)

OTHER PUBLICATIONS

International Search Report (PCT/ISA/210) issued on Aug. 26, 2008 by the Japanese Patent Office in its capacity as the International Searching Authority in International Application No. PCT/JP2008/061487.

(Continued)

*Primary Examiner* — Unsu Jung
*Assistant Examiner* — Nasir S Shahrestani
(74) *Attorney, Agent, or Firm* — Buchanan Ingersoll & Rooney PC

(57) ABSTRACT

An optical fiber is positioned in a lumen of a sheath so a gap exists between the sheath and optical fiber. A filling member fills part of the longitudinal extent of the gap and fixes the optical fiber. The gap is devoid of the filling member over a part of the longitudinal extent of the of the optical fiber so that an air gap exists between the optical fiber and the sheath. In the event bending, expansion and/or contraction are applied to the sheath, the stress is inhibited from being transmitted to the optical fiber. If the sheath is expanded and contracted, one end of the optical fiber is open and so the optical fiber is not expanded/contracted like the sheath expansion and contraction. Consequently, stress is not likely to be transmitted to the optical fiber and so it is possible to maintain a constant length of the optical fiber.

14 Claims, 13 Drawing Sheets

U.S. PATENT DOCUMENTS

| | | | |
|---|---|---|---|
| 2008/0228033 A1* | 9/2008 | Tumlinson et al. | 600/112 |
| 2009/0323076 A1* | 12/2009 | Li et al. | 356/479 |
| 2011/0230770 A1* | 9/2011 | Furnish | 600/478 |

FOREIGN PATENT DOCUMENTS

| | | |
|---|---|---|
| JP | 2000-321472 A | 11/2000 |
| JP | 2001-272332 A | 10/2001 |
| JP | 2002-250847 A | 9/2002 |
| JP | 2003-035660 A | 2/2003 |
| JP | 2004-191506 A | 7/2004 |
| JP | 2007-041568 A | 2/2007 |
| JP | 2007-075403 A | 3/2007 |

OTHER PUBLICATIONS

Written Opinion (PCT/ISA/237) issued on Aug. 26, 2008 by the Japanese Patent Office in its capacity as the International Searching Authority in International Application No. PCT/JP2008/061487.

* cited by examiner

10F

OPTICAL CABLE AND OPTICAL COHERENCE IMAGING DIAGNOSTIC APPARATUS USING THIS CABLE

This application is a continuation of International Application No. PCT/JP2008/061487 filed on Jun. 24, 2008, and claims priority to Japanese Application No. 2007-172932 filed on Jun. 29, 2007, the entire content of both of which is incorporated herein by reference.

TECHNICAL FIELD

The present invention generally relates to an optical cable or the like. The invention also generally relates to an optical coherence imaging diagnostic apparatus outfitted with an optical cable. More specifically, the disclosure here involves an optical cable or the like constructed to include an optical fiber main body and a sheath for protecting the main body, wherein the sheath is constructed so that even if an external stress such as a bending stress, expansion stress or contraction stress is applied to the sheath, the external stress is not applied to the optical fiber main body. Also, the cable is constructed so that it is difficult to exert influence on the expansion and contraction of the optical fiber main body.

BACKGROUND DISCUSSION

In the past, a catheter type imaging diagnostic apparatus has been widely used for diagnosing arteriosclerosis, for diagnosis before surgery on an occasion of an intravascular treatment by a balloon catheter and a high functional catheter such as a stent and the like, or for confirming results after surgery.

One example of an imaging diagnostic apparatus is an intravascular ultrasound diagnostic apparatus (IVUS: Intra-Vascular Ultra-Sound). Generally, the intravascular ultrasound diagnostic apparatus is a diagnostic apparatus which obtains vascular cross-section images, after an ultrasound transducer built-in probe is radially scanned in a blood vessel and a reflected wave (ultrasound echo) reflected by an intravascular biological tissue is received by the same ultrasound transducer, based on the strength of the ultrasound echo produced by applying an amplification process, detection or the like.

In addition, recently, in order to obtain cross-section images of higher resolution, there has been promoted a development of an optical coherence imaging diagnostic apparatus (OCT: Optical Coherent Tomography) which performs an imaging diagnosis by utilizing light coherence.

An optical coherence imaging diagnostic apparatus is a diagnostic apparatus in which reflected light from a specific point in the depth direction of the biological tissue is extracted by superimposing reflected light from the surface and the inside of a biological tissue when entering a low coherence measuring light (signal light) into the intravascular biological tissue and reference light which is obtained by dispersing the measuring light differently from that and whose light path length is in conformity therewith, and after converting that into an electric signal, a vascular cross-section image is obtained by converting it into image information.

In addition, recently there has been promoted also a development of an optical coherence imaging diagnostic apparatus utilizing wavelength scanning (OFDI: Optical Frequency Domain Imaging) which is an improvement type of optical coherence imaging diagnostic apparatus. The optical coherence imaging diagnostic apparatus utilizing wavelength scanning (OFDI) is a diagnostic apparatus in which reflected light from respective points in the depth direction of the biological tissue is extracted based on the differences of the frequency components by continuously changing wavelengths of the measuring light which enters an intravascular biological tissue, and vascular cross-section images are obtained by using the reflected light. In the case of the optical coherence imaging diagnostic apparatus utilizing wavelength scanning (OFDI), there is an advantage compared with an optical coherence imaging diagnostic apparatus (OCT) in that the moving portion for continuously varying the light path length of the reference light can be eliminated.

It is generally known that an optical fiber is used, for example, in a so-called optical coherence imaging diagnostic apparatus of the OCT and OFDI type, to transmit the measuring light. The optical fiber is an electric transmission line so referred to in an ultrasound imaging diagnostic apparatus, and the fiber is inserted into a driving shaft which transmits rotary driving force, and a portion of the fiber is fixed to the driving shaft.

In this optical coherence imaging diagnostic apparatus, a portion corresponding to the ultrasound transducer so referred to in the ultrasound imaging diagnostic apparatus is an optical component of a spacer, a rod lens and a prism or the like which is formed at a distal portion of the optical fiber. The light emanating from the optical fiber is focused by the aforesaid optical component and further, is emitted to the living body in a state of being bent in a direction approximately perpendicular with respect to the driving shaft.

Japanese Unexamined Patent Publication No. 2001-272332 and Japanese Unexamined Patent Publication No. 2003-35660 disclose that such an optical coherence imaging diagnostic apparatus can be constructed such that optical coherence images are produced, as mentioned above, by making a returned light (reflected light) obtained by illuminating a signal light to a living body which is a measuring object and a reference light interfere each other.

To generally explain this light path system, as shown in FIG. 20, a measuring light La emitted from a light source is split into a sample light Lo and a reference light Lr by a splitting unit (beam splitter) BS for splitting this measuring light La. The split sample light Lo is illuminated onto a biological tissue which is a measuring object. The returning sample light (returned light) Lo which is reflected from the biological tissue once again enters the beam splitter BS.

On the other hand, the reference light Lr split by the beam splitter BS is reflected by a reference mirror RM and again enters the beam splitter BS along the same light path. Here, it is designed such that the light path length (referred to as Lo) from the beam splitter BS to the biological tissue (surface thereof) and the light path length (referred to as Lr) from the beam splitter BS to the mirror RM will be approximately equal.

The reference light Lr entering into the beam splitter BS and the returned sample light Lo interfere optically, and the optically interfering light is enters a photo detector (photo diode) PD. Owing to a fact that the optically interfering light entering the photo detector PD is detected and demodulated, images of the tissue cross-section of the biological tissue can be obtained.

Japanese Unexamined Patent Publication No. 2000-321472 and Japanese Unexamined Patent Publication H8-262287 disclose an optical fiber arranged in a hollow of a flexible tube.

Though not explained in detail in FIG. 8 of Japanese Unexamined Patent Publication No. 2001-272332 and in FIG. 4 of Japanese Unexamined Patent Publication No. 2003-35660, the light path systems are coupled by optical fibers in order to obtain the optical coherence images mentioned above in connection with the optical coherence imaging diagnostic apparatus. Any of the light source, the optical fiber which is the light path from the light source to the beam splitter BS, the optical fiber which is the light path from the beam splitter BS to the reference mirror, and the reference mirror is housed in the main body of the imaging diagnostic apparatus (steering control device).

On the other hand, the optical fiber which handles the signal light for observing the biological tissue should be inevitably introduced to the outside of the optical coherence imaging diagnostic apparatus (hereinafter, referred to as apparatus main body) for a portion thereof. Also, in order to radially scan the biological tissue as mentioned above, it is necessary to insert and attach the driving shaft reached until the distal portion of the catheter sheath which goes into the inside of the biological tissue in the catheter sheath together with the optical fiber.

In order to transmit driving force to the driving shaft, there is mounted on the outside of the apparatus main body a scanner including a motor drive unit (depending on circumstances, a scanner having pullback function). With respect to the installation of this scanner, the optical fiber cable derived to the outside of the steering control device is coupled to the input terminal side of this scanner (which means the steering control device side). Then, the output terminal side of this scanner is coupled to the catheter device.

As mentioned above, the scanner usually has a construction separate from the steering control device and also, the optical fiber cable arranged between the scanner and the steering control device has one end coupled to the input terminal side of the scanner and concurrently an optical connector is mounted on the other end. Because this optical connector is coupled to the optical connector provided on the steering control device side, it is constructed so that the light path of the sample light Lo will be formed.

Also for the optical coherence imaging diagnostic apparatus without a scanner, it is not preferable for a catheter device which is disposable or for which disinfection is necessary every time to be directly mounted on a large-sized steering control device. It is preferable to employ a construction which is freely attachable and detachable with respect to the optical fiber cable for signal light extending from the apparatus and for that purpose, it is necessary also for the optical fiber cable derived to the outside of the apparatus main body to use an optical fiber cable.

In the case of image diagnosis performed using an optical fiber as in a case of this optical coherence imaging diagnostic apparatus, it is necessary to couple the space between the apparatus main body and the catheter device or the space between the apparatus main body and the scanner by using an optical fiber cable.

Here, for the optical fiber built-in in the optical fiber cable, there is used, as mentioned later, an optical fiber main body (optical fiber core line) composed of a core, a clad and a protection tube or an optical fiber main body (optical fiber core line) for which a buffer layer (silicone resin or the like) further intervenes between the clad and the protection tube. Alternatively, there is used a tensile strength type optical fiber main body (tensile strength type optical fiber core line) in which one of those optical fiber main bodies is further covered by a tensile strength fiber as a tension member and a tube for protection.

The optical fiber main body itself has weak tensile strength and even in a case of the tensile strength type optical fiber main body, it is not possible to obtain sufficient tensile strength. Thus, they are weak with respect to bending, expansion and contraction of the fiber. In particular, when the optical fiber main body is subjected to an applied expansion and contraction force, there is a fear that the optical fiber main body (in particular, the core line (core)) will slightly be expanded and contracted. When such expansion and contraction occur, the light path length handled for the sample light changes. In a case in which little change occurs in this light path length, the aimed interference cannot be obtained. In a worst case scenario, it becomes quite difficult, perhaps impossible, to obtain optical coherence images from the light after the earliest optical coherence.

Specifically, when the difference between the light path length (Lo) from the beam splitter BS to the biological tissue (surface thereof) and the light path length (Lr) from the beam splitter BS to the mirror RM exceeds around 5 mm to 7 mm, it becomes quite difficult, if not impossible, to obtain optical coherence images.

Consequently, with respect to the optical fiber wired on the outside of the apparatus main body, considerably cautious handling of the fiber must occur. However, as a practical matter, it is almost nearly impossible to perform a coupling operation (attaching, detaching operation) and a storing operation with respect to the optical coherence imaging diagnostic apparatus and further, to execute an actual diagnosis procedure or the like without applying stress (inclusive of bending, expansion and contraction or the like, hereinafter referred to as external stress) to the optical fiber handling the sample light at all.

Without realizing it, some sort of external stress is applied inevitably, and associated with this expansion of the optical fiber occurs. When such an external stress is applied, optical coherence images are disturbed. Consequently, it is necessary to exercise ingenuity such that the external stress will not be applied to the optical fiber.

Japanese Unexamined Patent Publication No. 2000-321472 and Japanese Unexamined Patent Publication H8-262287 disclose a construction in which an optical fiber is installed in a hollow of a flexible tube. With respect to the optical fiber used in the optical coherence imaging diagnostic apparatus, depending on the construction of the apparatus, it is necessary to provide an optical connector unit, but Japanese Unexamined Patent Publication No. 2000-321472 and Japanese Unexamined Patent Publication H8-262287 do not disclose a preferable structure for providing an optical connector unit.

SUMMARY

An optical cable includes a sheath possessing a lumen and an inner surface, an optical fiber located in the lumen of the sheath and possessing an outer surface, and a filling member. The lumen and the optical fiber are configured so that the inner surface of the sheath is spaced from the outer surface of the optical fiber over an entire longitudinal extent of the optical fiber. The filling member completely fills between the inner surface of the sheath and the outer surface of the optical fiber over less than the entire longitudinal extent of the optical fiber to fix in position the optical fiber. An air gap exists between the inner surface of the sheath and the outer surface of the optical fiber allowing the optical fiber to move relative to the sheath, with the air gap extending over a part of the longitudinal extent of the optical fiber devoid of the filling member.

According to another aspect, an optical coherence imaging diagnostic apparatus includes an optical connector for external input and output which inputs and outputs sample light within the sample light and a reference light which are produced in an optical coherence imaging diagnostic apparatus main body and which are used for optical coherence, and an optical cable which transmits the sample light to the measuring object side through the optical connector for external input and output and concurrently which transmits and introduces reflected light from the measuring object to the optical connector for external input and output. The optical cable comprises a sheath having a lumen, an optical fiber positioned in the lumen so that a longitudinally extending radial gap exists between an outer surface of the optical fiber and an inner surface of the sheath, and a filling member completely filling the radial gap over a part of the longitudinal extent of the radial gap to fix in place the optical fiber. An optical connector is provided on the filling member side of the optical cable for being coupled to the optical connector for external input and output.

As disclosed here, the optical fiber is positioned and attached (fixed) in a hollow sheath (sheath having a lumen) while maintaining an air gap. A portion of the optical fiber is fixed in the hollow sheath through a filling member, so that even if external stress of bending, expansion and contraction or the like is applied to the sheath side, the stress is not likely to be transmitted to the optical fiber inside. Even if the sheath for protection is slightly expanded under the influence of the expansion and contraction, one end of the optical fiber is open, so that the optical fiber will not be expanded and contracted corresponding to the expansion and contraction of the sheath. Consequently, there can be avoided a phenomenon in which an influence by an external stress is transmitted to the optical fiber. Thus, the length of the optical fiber can be maintained constant (inclusive of substantially constant).

Also, applying such an optical cable to an optical coherence imaging diagnostic apparatus, even if an external stress is applied during a working time of attaching or detaching this optical cable with respect to the apparatus, or during diagnosis, influence is not likely to be exerted to the optical fiber in the sheath. Consequently, the preset light path length for optical coherence can be maintained, so that it is possible to obtain accurate optical coherence images.

In the optical cable disclosed here, a construction is employed in which an optical fiber is located in a hollow sheath, with only a portion of the optical fiber being fixed on the sheath inner surface through a filling member.

By employing a structure in which a portion of the optical fiber is fixed on the sheath inner surface through the filling member, there can be obtained a structure in which the connection and the fixation of the optical fiber and the optical connector is relatively easy. Also, by inserting and providing the optical fiber in the hollow sheath, even if an external stress of bending, expansion and contraction or the like is applied to the sheath, there is little fear that the influence will be transmitted to the optical fiber inside. Even if the external stress is transmitted to the optical fiber, one end side of the optical fiber is open with respect to the sheath and therefore, it is not likely to happen that the external stress is directly transmitted to the optical fiber.

The optical cable mentioned above is used in an optical coherence imaging diagnostic apparatus so that even if an external stress is applied to the sheath during a working time of the attachment, detachment or the like of the optical cable, or during diagnosis, the influence to the optical fiber by the external stress can be avoided relatively reliably and therefore, there is obtained a feature in which the light path length of the optical fiber can be maintained to be a preliminarily defined light path length. Consequently, the apparatus is well suited to being able to provide excellent optical coherence images.

DETAILED DESCRIPTION

The following description of embodiments of an optical cable disclosed here, and an optical coherence imaging diagnostic apparatus embodying an optical cable, is discussed in the context of an optical coherence imaging diagnostic apparatus of the OCT type. However, the disclosure is also applicable to, for example, an optical coherence imaging diagnostic apparatus utilizing wavelength scanning (OFDI).

Figure 1:
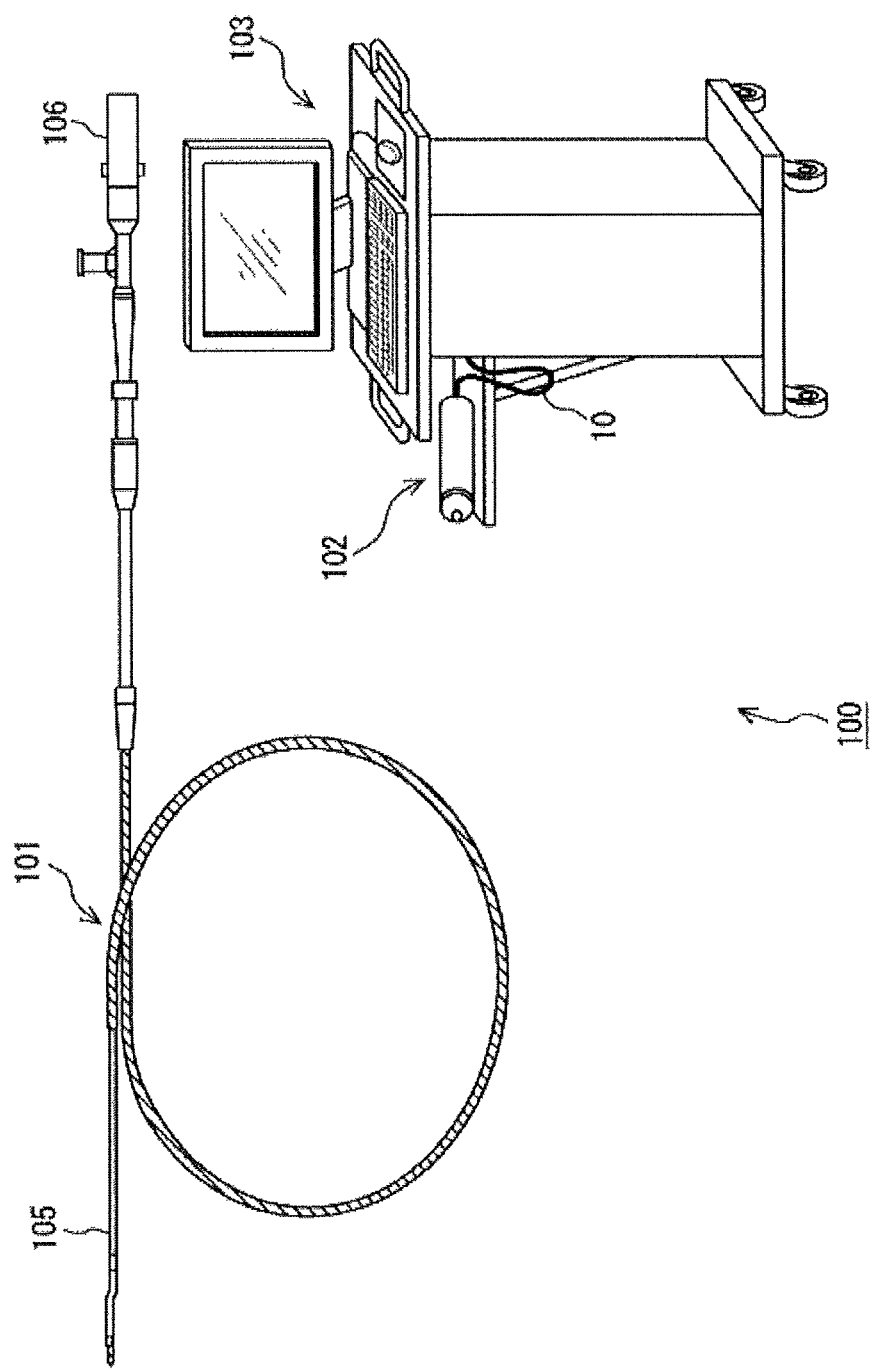
FIG. 1 is a diagram illustrating an optical coherence imaging diagnostic apparatus utilizing the optical cable disclosed here.

FIG. 1 is a diagram generally showing features of an optical coherence imaging diagnostic apparatus (OCT) 100 including a catheter device embodying an optical cable disclosed here.

This optical coherence imaging diagnostic apparatus 100 includes a catheter device 101, a scanner & pullback unit 102 and a steering control device 103. The scanner & pullback unit 102 and the steering control device 103 are connected by an optical cable 10.

Here, the optical cable is a cable constructed to include, as discussed below in more detail, a hollow sheath, an optical fiber positioned in this hollow sheath, and a filling member fixing one end of the optical fiber on the hollow sheath. The reason for fixing the optical fiber on the hollow sheath by way of the filling member is because influences caused by external stress applied to the optical cable should preferably be avoided. In addition, connection and fixation to an optical connector or the like will be possible.

The optical fiber can include, for example, an optical fiber main body (optical fiber core line) composed of a core, a clad and a protection tube as discussed more fully below, or an optical fiber main body (optical fiber core line) further including a buffer layer (made of silicone resin or the like) positioned or intervening between the clad and the protection tube. In the case of using a tensile strength type optical fiber main body (tensile strength type optical fiber core line) in which the optical fiber main body such as those mentioned above is covered further by a fiber for tensile strength and a tube for protection as a tensile strength type fiber.

In use, the catheter device 101 is inserted into a blood vessel directly and the intravascular condition is observed by using a reflected light of a measuring light which is emitted through an optical component (not shown). The scanner & pullback unit 102 is coupled to a hub 106 provided at one end of the catheter device 101.

Then, as discussed in more detail below, an optical connector unit which is installed at an end portion of a driving shaft in the hub 106 and an optical adaptor which is included in the scanner & pullback unit 102 are mutually connected. By operating a drive mechanism in the scanner & pullback unit 102, the driving shaft in the catheter device 101 is radially scanned.

The steering control device 103 is constituted by a control unit including a CPU and when executing an intravascular optical coherence imaging diagnosis, the control device functions to input various kinds of setting values and functions to process data obtained by a measurement and for displaying the data as a cross-sectional image.

Figure 2:
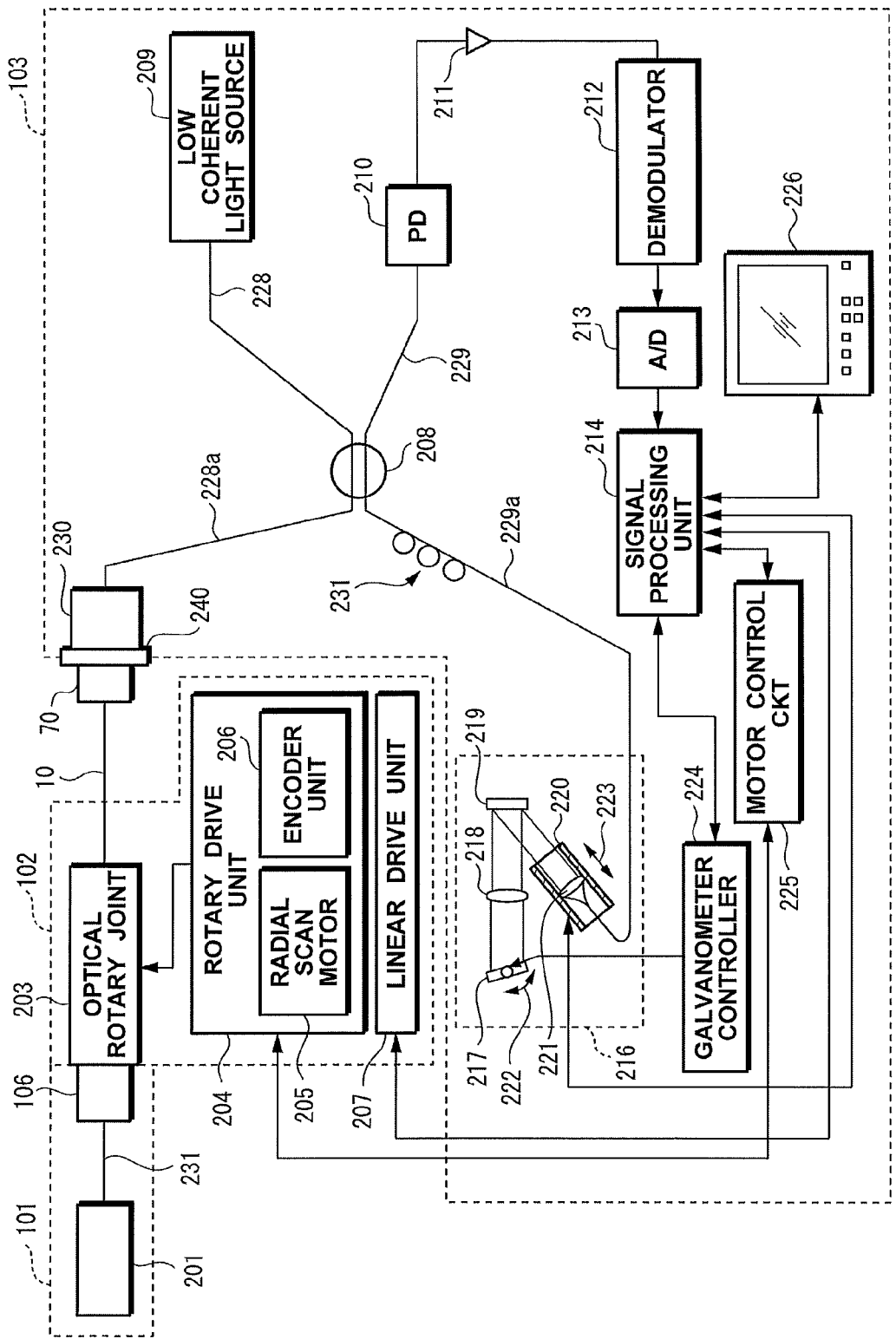
FIG. 2 is a block diagram illustrating features of the optical coherence imaging diagnostic apparatus, including a light path system.

FIG. 2 is a diagram schematically illustrating additional aspects and features of the steering control device 103 and the scanner & pullback unit 102 of the optical coherence imaging diagnostic apparatus 100 shown in FIG. 1.

A low coherence light source 209, for example a relatively high brightness light emitting diode or the like, has a wavelength of around 1310 nm and outputs a measuring light showing coherence only in a short distance range such that the coherence distance (coherence length) of the light is around a few μms to several tens μms.

For this reason, after splitting this light into two paths by an optical coupler unit (beam splitter BS), in a case in which this light is again superimposed, it is detected as a coherent light in a case in which the difference between the two light path lengths from the split point to the superimposed point is in a short range of around 17 μm as mentioned above, but it is not detected as a coherent light in a case in which the difference between the light path lengths is larger than that.

The following description describes a situation in which a measuring light obtained as a reflected light from a measuring object of a blood vessel or the like is a sample light and a measuring light obtained as a reflected light from a measuring object of a reference (reference object which is a measuring object) is a reference light. In a case in which the light path length Lo of the sample light and the light path length Lr of the reference light deviate by the amount of the coherence length or more at the split point, the images by the earliest optical coherence cannot be obtained and noises appear.

The light of the low coherence light source 209 enters one end of a first single mode fiber (optical fiber) 228 and is transmitted to the distal end surface side of the fiber. The first single mode fiber 228 is optically coupled with a second single mode fiber (optical fiber) 229 at an optical coupler unit 208. This optical coupler unit 208 functions as a beam splitter at which the light is split into two paths and transmitted.

An optical connector 230 provided on the distal side of the first single mode fiber 228a and on the distal side from the optical coupler unit 208 for the first single mode fiber 228 is coupled to an adaptor 240. The optical connector 230 is an example of an optical connector 230 for external input and output. Also, the adaptor 240 is coupled with an optical connector 70 provided on the optical cable 10. The optical cable 10 is a cable for coupling the steering control device 103 and the scanner & pullback unit 102 provided outside the device.

For this optical cable 10, other than a case in which there is used a cable constituted by an optical fiber for transmitting only the sample light, a compound optical cable is preferably used. This compound optical cable is formed by integrating an electric cable (signal line) used when driving a rotation mechanism in the scanner & pullback unit 102 or the like, a control signal line transmitting a control signal for controlling the catheter device 101 and the like with an optical fiber.

The scanner & pullback unit 102 is provided, as shown in FIG. 2, with an optical rotary joint 203 for transmitting the light while coupling a portion between a non-rotation portion (steering control device 103 side) and a rotation portion (catheter device 101 side).

On the distal side (rotation portion side) in the optical rotary joint 203, there is coupled an optical connector provided on the catheter device 101 in a freely attachable and detachable manner. Owing to this coupling, it is possible to transmit the sample light from the low coherence light source 209 through the optical cable 10 with respect to a third single mode fiber (optical fiber) 231 which is connected with an optical component 201 provided at the distal portion of the catheter device 101 and which is rotatingly drivable.

The light transmitted to the third single mode fiber 231 is illuminated while being radially scanned from the distal side of the optical component 201 to the biological tissue side in a coelom. Consequently, the rotation portion side of the optical rotary joint 203 is rotatingly driven depending on a radial scan motor 205 of a rotary drive unit 204. Also, a motor control circuit 225 is connected to the radial scan motor 205 and is controlled by a signal processing unit 214, and the rotation driving of the radial scan motor 205 is controlled.

A portion of the reflected light which is scattered on the surface or at the inner portion of the biological tissue side is taken-in by the optical component 201 and is returned toward the fiber cable 10 and the first single mode fiber 228a through a reverse light path. A portion of the returning light is split onto the second single mode fiber 229 side by the optical coupler unit 208 and enter a photo detector (for example, photodiode) 210 from the second single mode fiber 229 end. The rotation angle of the radial scan motor 205 is detected by an encoder unit 206.

The scanner & pullback unit 102 includes a linear driving motor 207 as a linear drive unit for pullback. Based on instructions from the signal processing unit 214, there is defined the operation (movement in driving axis direction) of the insertion direction (distal direction and its opposite direction in the coelom) of the catheter device 101. The movement in the driving axis direction is realized by the fact that the linear driving motor 207 operates based on a control signal from the signal processing unit 214.

A variable light-path-length mechanism 216 for varying the light path length of the reference light is provided on the side of a fiber on the distal side (referred to as distal side optical fiber) 229a from the optical coupler unit 208 for the second single mode fiber 229.

The variable light-path-length mechanism 216 includes first light path length changing means for changing in a high-speed manner the light path length corresponding to inspection range in the depth direction of the biological tissue, and second light path length changing means for absorbing fluctuation of the light path length depending on individual differences of the devices.

Facing the distal end of the distal side optical fiber 229a is arranged a grating (diffraction lattice) 219 through a collimating lens 221 which is mounted on one axis stage 220 together with the distal end and which is freely movable in the direction shown by an arrow 223. Also, a galvanometer mirror 217, which is rotatable within a minute angle through a lens 218 facing this grating 219, is mounted as the first light path length changing means. This galvanometer mirror 217 is rotatingly driven in the direction of the arrow 222 in a high-speed manner by a galvanometer controller 224.

The galvanometer mirror 217 is a mirror for reflecting the light by a galvanometer mirror and functions as a reference mirror. It is constructed such that by applying an alternate driving signal to the galvanometer, the galvanometer mirror 217 attached on the moving portion thereof can rotate (pivot) in a high-speed manner.

In other words, owing to the fact that a driving signal is applied to the galvanometer mirror 217 from the galvanometer controller 224 and the mirror rotates in a high-speed manner in the direction of the arrow 222 by the aforesaid driving signal, a state occurs in which the light path length of the reference light (standard light) changes in a high-speed manner by an amount of the light path corresponding to the inspection range in the depth direction of the biological tissue.

On the other hand, the one axis stage 220 forms the second light path length changing means. This one axis stage 220 also functions as an adjusting means for adjusting an offset.

The light (reference light) whose light path length is changed by the variable light-path-length mechanism 216 is superimposed with the light (sample light) which is leaked from the first single mode fiber 228a side at the optical coupler unit 208 provided on the way of the second single mode fiber 229, and the coherent light thereof is light-received by the photo diode 210.

The light (coherent light) light-received by the photo diode 210 is photoelectrically converted, is amplified by an amplifier 211 and thereafter, is inputted to a demodulator 212. In this demodulator 212, there is performed demodulation processing for extracting only the signal portion of interfering light and the output thereof is inputted to an A/D converter 213.

In the A/D converter 213, there are produced digital data (coherent light data) of one line by sampling the coherent light signal for the amount of 200 points. The sampling frequency is a value obtained by dividing one scanning time of the light path length by 200.

The coherent light data of one line unit, which are produced by the A/D converter 213, are inputted to the signal processing unit 214. In this signal processing unit 214, a cross-sectional image is formed for each position in the blood vessel by converting the coherent light data of the depth direction to an image signal, and this image signal is outputted to an LCD monitor 226 by fixed frame rate.

The signal processing unit 214 is connected with the galvanometer controller 224 for controlling the scanning of the light path length of the galvanometer mirror (reference mirror) 217, the galvanometer controller 224 outputs a driving signal to the signal processing unit 214 and the motor control circuit 225 executes the control based on this driving signal such that the radial scan is to be performed while synchronizing with the galvanometer mirror 217.

Figure 3:
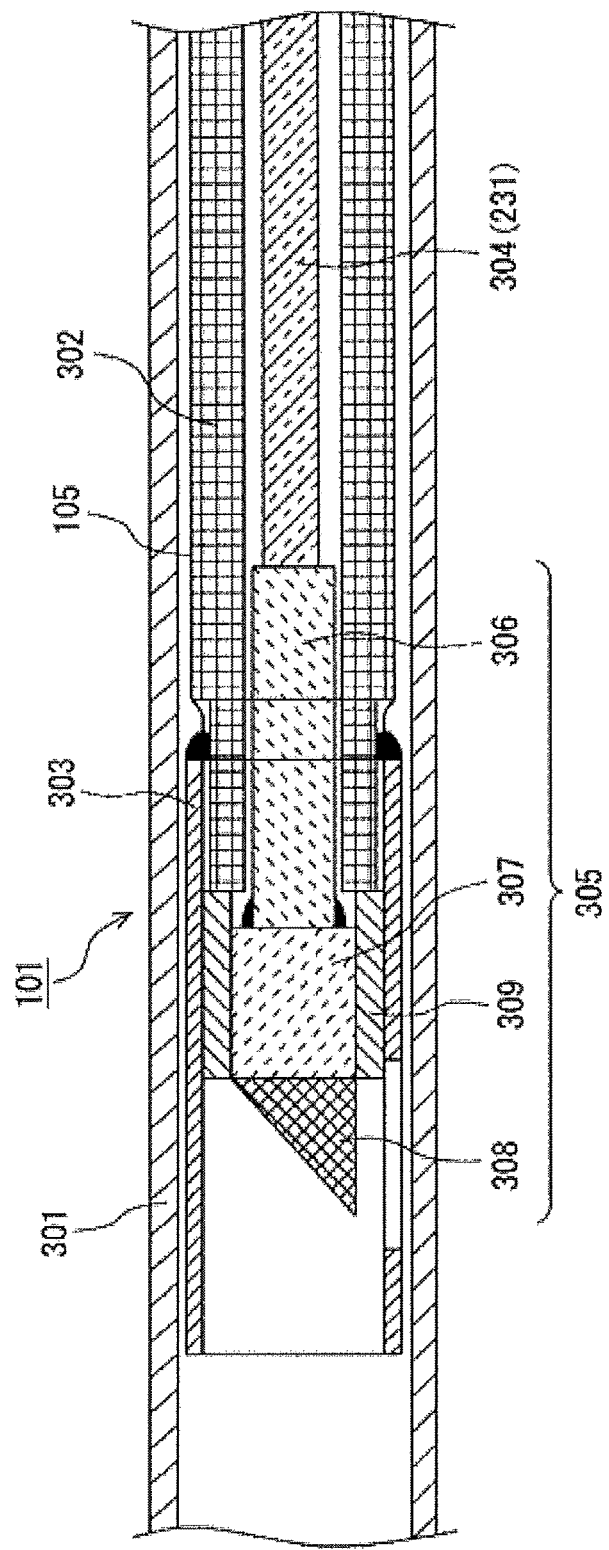
FIG. 3 is a cross-sectional view of a distal portion of a catheter device.

FIG. 3 is a cross-sectional view of a distal portion of a driving shaft 105 of the distal portion of the catheter device 101 as seen from the lateral direction. As shown in FIG. 3, the distal portion of the catheter device 101 includes the driving shaft 105 positioned in the catheter sheath 301.

The driving shaft 105 includes a coil shaft 302 having a multi-layer relatively tightly-wound coil structure and a housing 303 fixed on the distal side of the coil shaft 302. The third single mode fiber 231 (hereinafter, referred to as "optical fiber 304") is positioned inside the coil shaft 302, and a first optical component 305 is mounted at the distal portion of the optical fiber 304. The first optical component 305 emanates and focuses light beams, and bends (redirects) them in the perpendicular direction (inclusive of approximately perpendicular direction). The first optical component 305 is comprised of a spacer 306, a selfoc lens 307 and a prism 308.

The distal portion of the driving shaft 105 is provided with a contrast marker 309 for making it possible to confirm the position of the distal portion of the driving shaft 105 under x-ray fluoroscopy.

The mounting of the first optical component 305 can be achieved by adhesion depending on the adhesive agent, for example one having high handling ability such as an ultraviolet curing type adhesive agent and the like, or by a melting connection method through use of an optical fiber melting connection machine.

Figure 4:
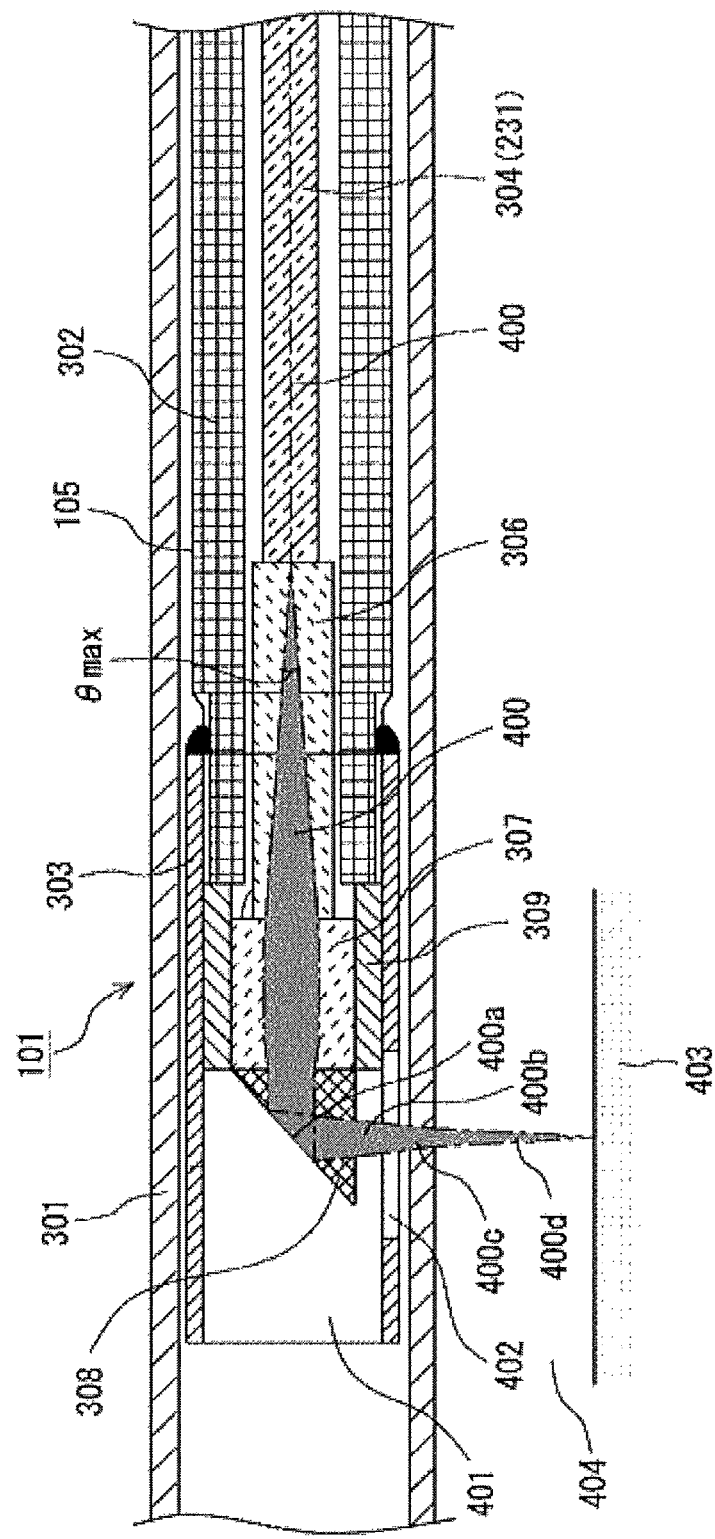
FIG. 4 is a cross-sectional view similar to that of FIG. 3, but with a light path taken into account.

FIG. 4 schematically illustrates a light beam trajectory when the light beam is transmitted in the optical fiber 304 of FIG. 3. The optical fiber 304 is composed of a core which is a central portion having a high refractive index, a clad which is located around the core and which has a lower refractive index compared with that of the core, and a protection tube which covers this clad. The refractive index of the clad can be lower by as much as 1% compared with that of the core. A light beam 400 is transmitted along the boundary surface between the core and the clad portion while being totally reflected.

The light beam reaching the distal portion of the optical fiber 304 is emanated in the spacer 306 connected adjacent the distal end of the fiber 304. The light beam 400 emanating in the spacer 306 is refracted in the selfoc lens 307 which is connected adjacent to the spacer 306 and becomes a focused light beam.

The focused light beam 400a is bent by the prism 308 in the perpendicular direction or at a right angle (inclusive of approximately perpendicular and approximately at a right angle). It becomes a light beam 400b by being refracted on the boundary surface between the prism 308 and the medium (air) and passes through an aperture portion 402 of the housing 303.

The light beam 400b which passes through the aperture portion 402 is refracted at the boundary surface between the medium (air) 401 and the catheter sheath 301 and becomes a light beam 400c. The light beam 400c is refracted at the boundary surface between the catheter sheath 301 and a medium (physiological saline water replacing blood) 404 and becomes a light beam 400d, and after passing through the medium (physiological saline water replacing blood) 404, the beam is illuminated on biological tissue 403 of a blood vessel or the like.

The light reflected at the biological tissue 403 is, as mentioned above, returned to the optical cable 10 side through the optical connector in the hub 106 and the optical rotary joint 203 while following the same light path. Further, the light arrives at the optical coupler unit 208 as a signal light (sample light) through the optical connectors 70, 230 and the first single mode fiber 228a.

As mentioned above, it is not possible for the diagnostic apparatus which executes the diagnosis of the images by utilizing such an optical coherence to produce images from the correct coherent light, in particular if the light path length of the sample light Lo and the reference light Lr do not coincide. Given that the reference light Lr is obtained from the second single mode fiber 229 which is housed in the steering control device 103, and the sample light Lo is obtained through the optical cable 10 (or compound optical cable) and the catheter device 101 which are connected to the steering control device 103 externally, a little expansion and contraction of the optical fiber in the optical cable 10 and the catheter device 101 can become a problem.

The optical fiber 304 in the catheter device 101 is protected by the coil shaft 302 and so the expansion and contraction of the optical fiber is not typically a big problem. On the other hand, the steering control device 103 which is a diagnostic apparatus main body and the scanner & pullback unit 102 are coupled by the optical cable 10, and the scanner & pullback unit 102 is constructed such that it can be used even at a place apart from the steering control device 103, and so an external stress of bending, expansion, contraction or the like is easily applied to this optical cable 10 when using a cable.

Even in the case of an optical fiber of any structure from the optical fiber main body and the tensile strength type optical fiber main body mentioned above, if the external stress is applied, expansion or contraction happens comparatively easily. When the expansion and contraction of the optical cable occurs during mounting work or during usage (during obtaining optical coherence images) of the optical cable 10, the optical coherence distance changes. When the optical coherence distance changes, in the worst case, it becomes impossible, in the earliest variable light-path-length mechanism 216, to absorb the expansion thereof or the like. Thus, a situation may arise in which coherent images cannot be obtained. Consequently, it is preferable to use an optical cable 10 which can avoid influences on the optical fiber even when an external stress is applied.

The optical cable 10 of this embodiment is constructed so that the optical fiber is protected from the external stress. One example of the optical cable 10 which can reduce or avoid influences of external stresses is described below.

Figure 5:
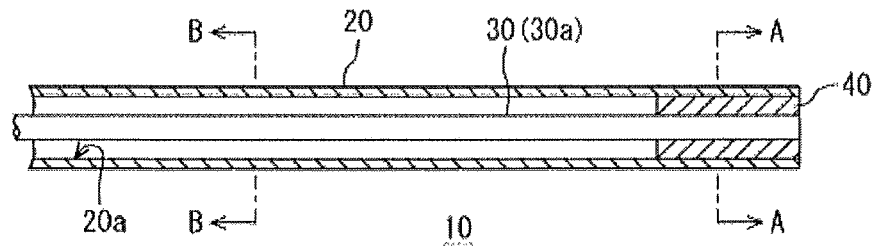
FIG. 5 is a longitudinal cross-sectional view of a portion of an optical cable disclosed here.

FIG. 5 illustrates an optical cable 10 according to one embodiment in which the usage is not limited. The optical cable 10 includes a hollow sheath for protection (inside sheath) 20, an optical fiber 30 inserted and attached in the hollow sheath and a filling member 40 which fixes a portion of the optical fiber 30 on the inside of the sheath 20.

The sheath 20 can be a resin tube having flexibility to such an extent as not to be deformed easily. The optical fiber 30 is positioned and attached in the lumen of this hollow sheath 20 while maintaining a predetermined air gap between the inner periphery or inside surface of the hollow sheath 20 and the outer periphery or outside surface of the optical fiber 30.

With respect to the optical fiber 30, as mentioned above, it is possible to use any one of several optical fiber main bodies 30a. For example, the optical fiber main body 30a can be comprised of a core, a clad covering the core, and a protection tube covering the outer circumferential surface of the clad. Alternatively, the optical fiber main body 30a can be comprised of a core, a clad covering the core, a protection tube outside the clad, and a buffer layer (made of, for example, silicone resin) interposed between the clad and the protection tube. Further, it is possible to use as the optical fiber main body 30a a tensile strength type optical fiber main body (optical fiber cord) which is covered by a tensile strength fiber (tension member) and a protection tube on the outside of this optical fiber main body 30a.

Figure 6:
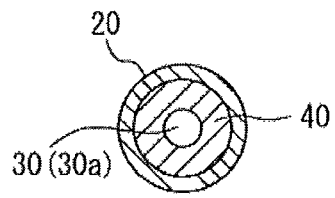
FIG. 6 is a cross-sectional view taken along the section line VI-VI in FIG. 5.
Figure 7:
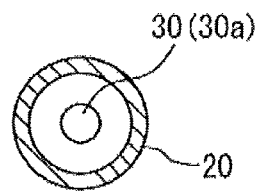
FIG. 7 is a cross-sectional view taken along the section line VII-VII FIG. 5.

The example shown in FIG. 5, as is clear also from the cross-sectional views of FIGS. 6 and 7, employs an optical fiber 30 in which the optical fiber main body 30a does not have the tensile strength fiber or the like.

The outer diameter of the optical fiber 30 is smaller than the inner diameter of the sheath 20, and the difference in the diameters is preferably selected such that a sufficient hollow space or gap is provided. As one example, when a fiber whose outer diameter is around 0.8 mm is used for the optical fiber 30, a tube having an inner diameter of around 3.0 mm is used as the sheath 20.

A portion of the optical fiber 30 is fixed in the sheath 20 by the filling member 40 as shown in FIG. 5 and FIG. 6. This is because it is necessary for the optical fiber 30 to be positioned in, attached and fixed to the sheath 20. Also, this is for making it possible to connect the optical fiber to an optical connector or the like.

In this example, the filling member 40 is filled on the right end side of the sheath 20 to fix the optical fiber 30 on the sheath 20. The other side of the optical fiber 30 is devoid of a filling member and is thus open as generally seen from FIG. 7. The filling member 40 can be, for example, a resin, an adhesive agent or a tensile strength fiber.

By inserting and attaching the optical fiber (optical fiber main body) 30 in the hollow air gap 20a in the sheath 20, fixing a portion of the optical fiber 30 on the sheath 20 through the filling member 40, and concurrently forming the optical cable 10 so that the other side of the sheath is opened in the air gap (i.e., is exposed or uncovered), it is possible that even if external stress is applied to the sheath 20, the influence of the stress is not applied to the optical fiber 30 in the inside.

Figure 8:
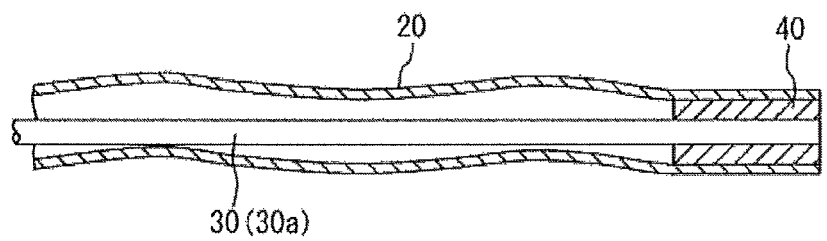
FIG. 8 is a longitudinal cross-sectional view of a portion of the optical cable in a use state.

For example, as shown in FIG. 8, even when external stress is applied to the sheath 20 so that the sheath 20 moves like a wave, it is difficult for the external stress to be transmitted to the optical fiber 30. In addition, when there is applied an external stress by which the sheath 20 may be expanded, it happens that also the sheath 20 is expanded slightly, but even if the sheath 20 is expanded, this expansion will not be applied to the optical fiber 30 and the optical fiber will not be expanded.

Figure 9:
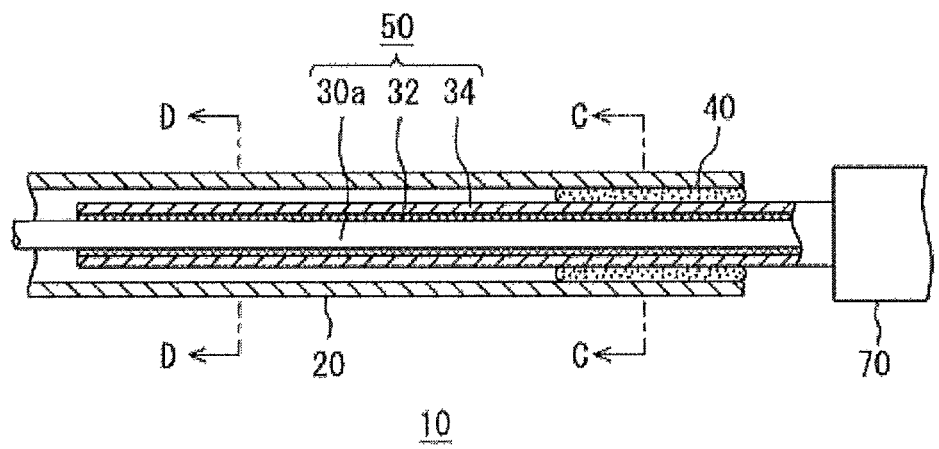
FIG. 9 is a longitudinal cross-sectional view of a portion of an optical cable according to another embodiment disclosed here.
Figure 10:
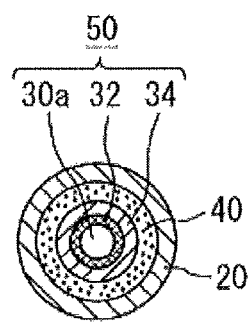
FIG. 10 is a cross-sectional view taken along the section line X-X in FIG. 9.

FIG. 9 illustrates an embodiment of the optical cable 10' in which a tensile strength type optical fiber is used as the optical fiber. The tensile strength type optical fiber involves a linear shaped body in which the outside of the optical fiber main body 30a is covered by a tensile strength fiber (tension member) 32, and a protection tube 34 covers the optical fiber main body 30a and the tensile strength fiber to form the tensile strength type optical fiber 50.

As shown in FIG. 9, in the case of the optical cable 10' incorporating the tensile strength type optical fiber 50, a sheath 20 having an inner diameter larger than the outer diameter of the tensile strength type optical fiber 50 is used. Concurrently, the optical cable 10' is constituted by this sheath 20 and the filling member 40 which fills in a portion of the space between the outer surface of the optical fiber 50 and the inner surface of the sheath 20. By virtue of this filling member 40, one end of the optical fiber 50 is fixed on the inner surface of the sheath 20.

Figure 11:
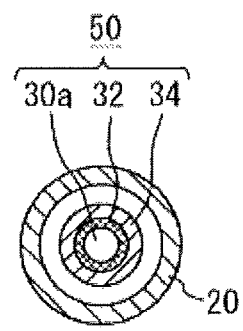
FIG. 11 is a cross-sectional view taken along the section line XI-XI in FIG. 9.

The filling member 40 is, as shown in the drawing, filled completely only in an axial portion of the inner surface of the sheath 20. That is, an axial portion of the space between the outer surface of the optical fiber 50 and the inner surface of the sheath 20 is completely filled with the filling member, while the remainder of the space between the outer surface of the optical fiber 50 and the inner surface of the sheath 20 is devoid of any filling member. The axially extending portion(s) of the space not filled with the filling member become air gaps as generally shown in FIG. 11.

The filling member 40 can be in the form of an adhesive agent or the like as mentioned above.

In this manner, in case of the optical cable 10' in which the optical fiber 50 is fixed on the end surface side of the sheath 20 by using the filling member 40, it is possible, as shown in FIG. 9, to use the cable by directly connecting the optical connector 70 or the like to the optical fiber 50 on the side for which the optical fiber main body 30a is fixed on the sheath 20 inner surface by the filling member 40.

Although the sheath 20 and the optical connector 70 are not fixed in FIG. 9, it is also possible to employ a arrangement in which the end surface of the sheath 20 closest to the connector 70 is extended, and the extended end portion of the sheath 20 is connected and fixed to the optical connector 70.

Even if such a tensile strength type optical fiber 50 is used, a predetermined air gap is produced between the sheath 20 and the tensile strength type optical fiber 50, so that there is obtained a cross-section as shown in FIG. 9 and the optical fiber 50 can be arranged in a predetermined hollow. Consequently, the optical fiber 50 can be protected relatively securely from external stress applied to the sheath 20.

Figure 12:
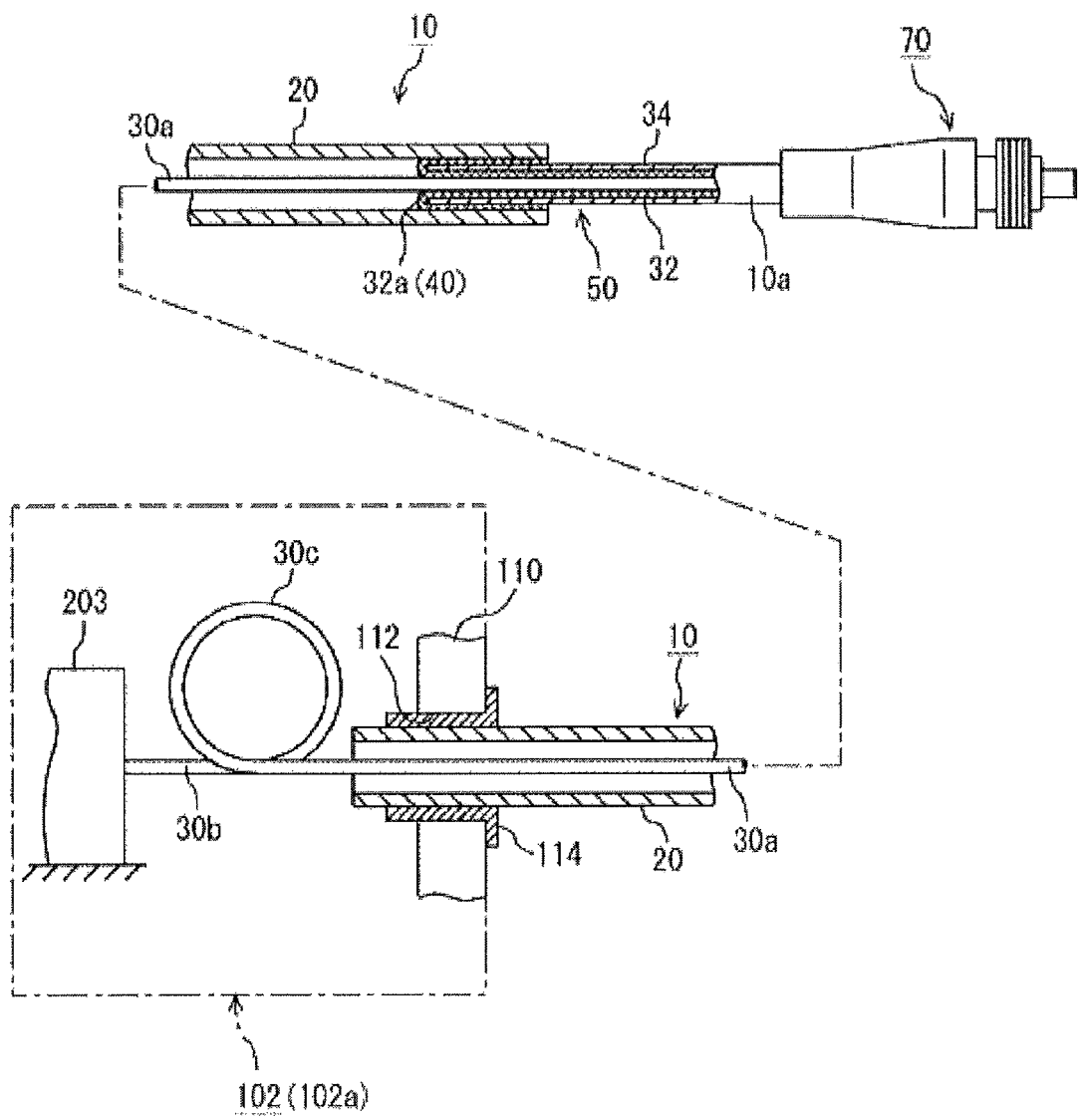
FIG. 12 is a partial longitudinal cross-sectional view showing the optical fiber of FIG. 9 applied to an optical coherence imaging diagnostic apparatus.

FIG. 12 shows a case in which a tensile strength type optical cable 10' is applied to a signal line for the optical coherence imaging diagnostic apparatus 100 shown in FIG. 2. Therefore, the scanner & pullback unit 102 is positioned on the left side of FIG. 12. In addition, the steering control device 103 which is a main body of the imaging diagnostic apparatus 100 is to be positioned on the right side thereof. The right end side of the optical cable 10' is provided with the optical connector 70. The illustrated embodiment shows the tensile strength type optical fiber 50 being used for the optical cable 10'.

To connect the optical connector 70 to the end portion of the optical cable 10', the optical fiber 50 in the optical cable 10' is extended to the optical connector 70 side. Although the tensile strength type optical fiber is used for the optical fiber 50 in the optical cable 10', the tensile strength fiber 32 and the protection tube 34 are respectively covered only in the space between the sheath 20 and the optical connector 70 as illustrated.

With a construction in which the tensile strength fiber 32 is covered in the space between the protection tube 34 and the optical fiber main body 30a, it is possible to achieve a strength suitable for attaching the optical connector 70. Also, as discussed below in more detail, a portion of the tensile strength fiber 32 serves as the filling member 40 so that the connection and fixation of the optical fiber 50 and the optical connector 70 is facilitated or made possible by this filling member 40.

The portion of the optical fiber main body 30a up to the right end portion of the interior (hollow) of the sheath 20 is covered by the tensile strength fiber 32 and the protection tube 34 as shown in FIG. 12. In addition, a free end portion 32a of the tensile strength fiber 32 is folded back to the outside surface of the protection tube 34 to cover and contact the outside surface of the protection tube 34. This folded-back free end portion 32a functions as the filling member 40. Thus, the portion of the protection tube 34 lying within the sheath 20 is covered on both its inner surface and its outer surface by respective portions of the tensile strength fiber 32. The hollow inner portion of the sheath 20 other than the right end portion of the sheath 20 is hollow other than for the optical fiber main body 30a. Thus, hollow inner portion of the sheath 20 other than the right end portion of the sheath 20 is devoid of both the tensile strength fiber 32 and the protection tube 34 which are peeled off or removed from the tensile strength fiber 32 or are nonexistent.

The other end of the optical cable 10', that is the left end portion, is connected to the scanner & pullback unit 102. Consequently, in this example, the sheath 20 of the optical cable 10' is inserted, attached and fixed to a through-hole 112, which perforates or passes through a frame portion 110 constituting a housing 102a of the scanner & pullback unit 102. The sheath 20 is attached and fixed through a fixation member 114. A distal portion 30b of the optical fiber main body 30a in the sheath 20 is coupled to the optical rotary joint 203, fixed on the inside of the frame portion 110, while being provided with a redundant line portion 30c.

The redundant line portion 30c of the optical fiber main body 30a is a surplus line portion for making it possible to absorb external stress even when external stress (for example, expansion and contraction) is applied to the optical fiber 30. Consequently, the redundant line portion 30c is housed in the frame portion 110 in a free state.

In this manner, the end portion of the sheath 20 of the optical cable 10' is fixed on the scanner & pullback unit 102 side and the one end portion (right end portion) of the sheath 20 is fixed on the optical connector 70 side. At that time, the optical fiber 50 is fixed only on the right end side of the sheath 20 and the distal portion 30b of the optical fiber 50 is coupled to the optical rotary joint 203 mechanically and optically.

Here, it is to be understood that the light path length (fiber length) in which the sample light Lo is transmitted and the light path length (fiber length) in which the reference light Lr is transmitted are selected so as to be equal to each other including the redundant line portion 30c and the third single mode fiber 231 which function as the redundant line portion provided at the single mode fiber 228a.

With this construction, even if external stress is applied to the sheath 20 constituting the optical cable 10' during a working time of the attachment or the detachment of the imaging diagnostic apparatus 100 with respect to the optical cable 10', during the storing operation or during the usage of the optical cable 10' (while obtaining diagnosis images), the external stress is seldom applied to the optical fiber 50 in the sheath 20.

In particular, even if there is applied an external stress so as to expand the sheath 20, the external stress is not transmitted to the optical fiber 50. Even if the external stress is supposedly transmitted to the optical fiber 50, one end side of the optical fiber 50 is open (not fixed), and so it is unlikely that a state will occur in which expansion of the optical fiber 50 is maintained. As a result, it is possible for the light path length of the sample light including the optical cable 10 to be maintained always as the defined length.

Figure 13:
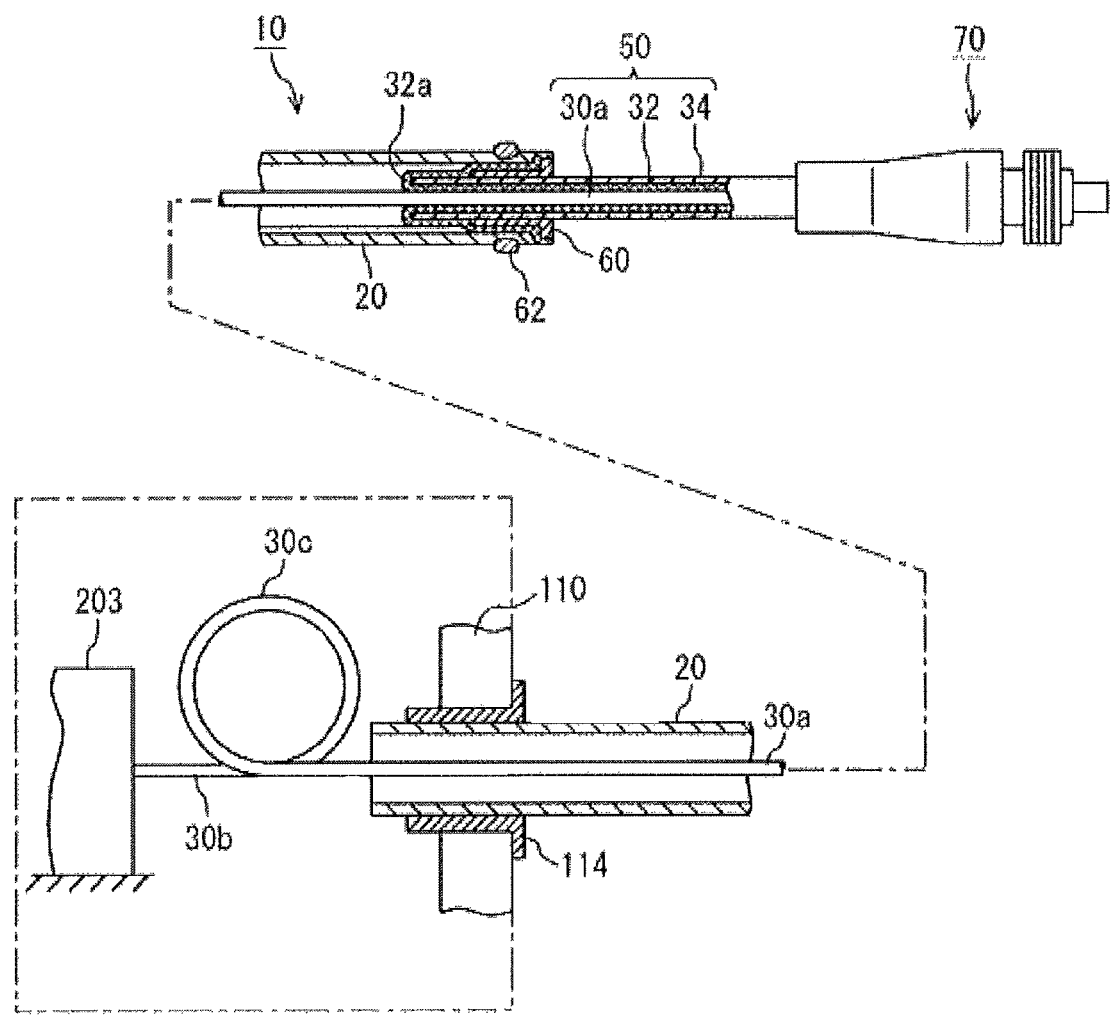
FIG. 13 is a partial longitudinal cross-sectional view showing an example of a connector connection when using an optical cable disclosed here.

FIG. 13 shows a modified example of FIG. 12. FIG. 13 shows an optical cable 10" with one example of fixation means for the filling member 40 which fills the space between the sheath 20 and the optical fiber 50 and for the sheath 20. Generally speaking, this example involves the optical fiber 50 being fixed to the sheath 20 by caulking.

More specifically, a metal ring 60 having a flange (the metal ring is a tubular member with a greater axial extent than the flange) is positioned as shown in FIG. 13 and is attached to the outer surface of the protection tube 34 which faces the right end surface of the sheath 20. The free end portion 32a of the tensile strength fiber 32 is turned back upon itself so that the metal ring 60 is surrounded by the fiber 32. That is, a portion of the tensile strength fiber 32 is positioned radially inwardly of the inner surface of the tube 60 (with the protection tube 34 interposed) and another portion of the tensile strength fiber 32 (i.e., the free end portion 32a) is positioned radially outwardly of the outer surface of the tube 60 so that the free end portion 32a of the tensile strength fiber 32 borders and contacts the outer surface of the tube 60. These two portions of the tensile strength fiber 32 axially overlap the tube 60. The right end portion of the sheath 20 is positioned to surround the free end portion 32a as illustrated, and in this condition, caulking is performed by using a metal ring 62 from the outer circumferential surface of the right end portion of the sheath 20.

By doing this, it is possible to fix one end of the optical fiber 50 at the right end portion of the sheath 20 reliably through the filling member 40 (32a). Other aspects of the optical fiber are the same as those of FIG. 12 and so the explanation of those aspects is not repeated.

In the embodiments described above, the optical cable is described in the context of an optical cable comprising a single body. However, other embodiments are possible. For example it is possible to use a compound optical cable constructed by twisting the present optical cable together with an electric-power transmitting electric cable for driving a control signal, a motor or the like, an example of which will be discussed below.

Figure 14:
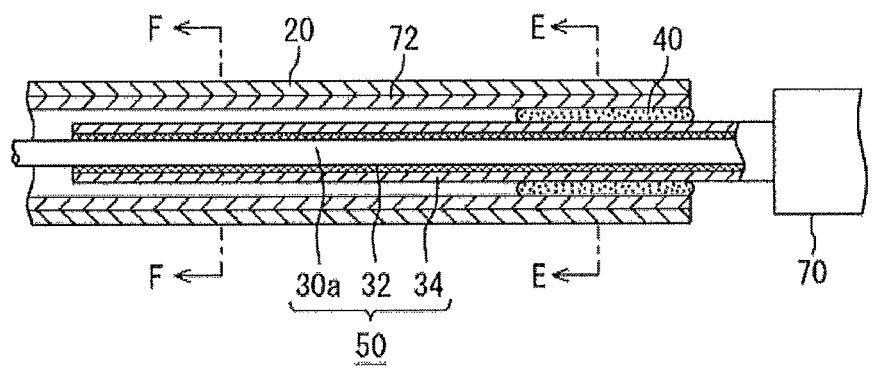
FIG. 14 is a longitudinal cross-sectional view of a portion of an optical cable according to another embodiment.
Figure 15:
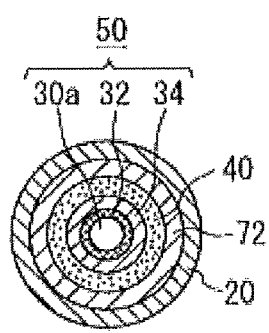
FIG. 15 is a cross-sectional view taken along the section line XV-XV in FIG. 14.
Figure 16:
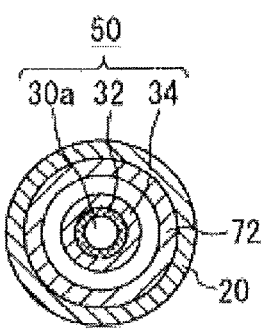
FIG. 16 is a cross-sectional view taken along the section line XVI-XVI in FIG. 14.

FIGS. 14-16 show another embodiment of the optical cable 210 disclosed here. The example of the optical cable 210 shown in FIGS. 14-16 includes a resin tube 72 intervening or positioned between the optical fiber 30/50 and the sheath 20, and concurrently the optical connector 70 is connected.

This embodiment of the optical cable utilizes, for the optical fiber, the tensile strength type optical fiber 50 in which the optical fiber main body 30a is covered by the tensile strength fiber 32 and the protection tube 34. On the one end of the optical fiber 50, the filling member 40 fills the space between the outer surface of the optical fiber 50 and the inner surface of the resin tube 72.

The resin tube 72 is positioned between the optical fiber 50 and the sheath 20 and is fixed in place. The resin tube 72 is a tube having an inner diameter larger than the outer diameter of the optical fiber 50, and an outer diameter approximately equal to the inner diameter of the sheath 20. Therefore, in the illustrated embodiment, the resin tube 72 contacts the inner surface of the sheath 20.

The resin tube 72 is preferably a tube of a material which exhibits slippery characteristics so that the surfaces of the tube are slippery and which has an abundance of flexibility such as a nylon tube. In this example, the optical fiber 50 and the sheath 20 have the same diameters as those in FIG. 5 so that, as illustrated in the respective cross-sectional views in FIG. 15 and FIG. 16, the radial space or gap (air gap) between the outer surface of the optical fiber 50 and the inner surface of the resin tube 72 is comparatively narrow.

Even in a situation such as this in which the radial gap or space is relatively narrow, the presence of the resin tube 72 makes it possible to inhibit or prevent applied external stress from adversely influencing the optical fiber 50 with respect to the sheath 20 also by the resin tube 72 other than by this sheath 20 itself.

The filling member 40 is preferably an adhesive agent. By using an adhesive agent, it is possible to connect the optical connector 70 (see FIG. 9) to the optical fiber 50 end surface on the side of the sheath filled with the filling member 40.

The embodiment of FIG. 14 is an example of an embodiment of the optical cable 210 in which only the optical fiber 50 is coupled to the optical connector 70. It is possible, for example, to extend the respective end surfaces of the resin tube 72 and the sheath 20 toward the optical connector 70 side and to couple and fix the extended end edges of the tube 70 and the sheath 20 to the optical connector 70 respectively. By way of example, it is possible to integrate the respective extended end edges, for example by molding, so as to be buried in the optical connector main body.

The optical fiber can also be in the form of an optical fiber 30 which is not of the tensile strength type. For the filling member 40, as mentioned above, it is possible to use a caulking member or the like together with an adhesive agent.

The filling member 40 can also be provided as a part of the tensile strength fiber 32 in a manner similar to that described above. For instance, the end surface side of the tensile strength fiber 32 can be folded back onto the outer circumferential side of the protection tube 34. This folded-back free end portion of the tensile strength fiber 32 constitutes the filling member.

Figure 17:
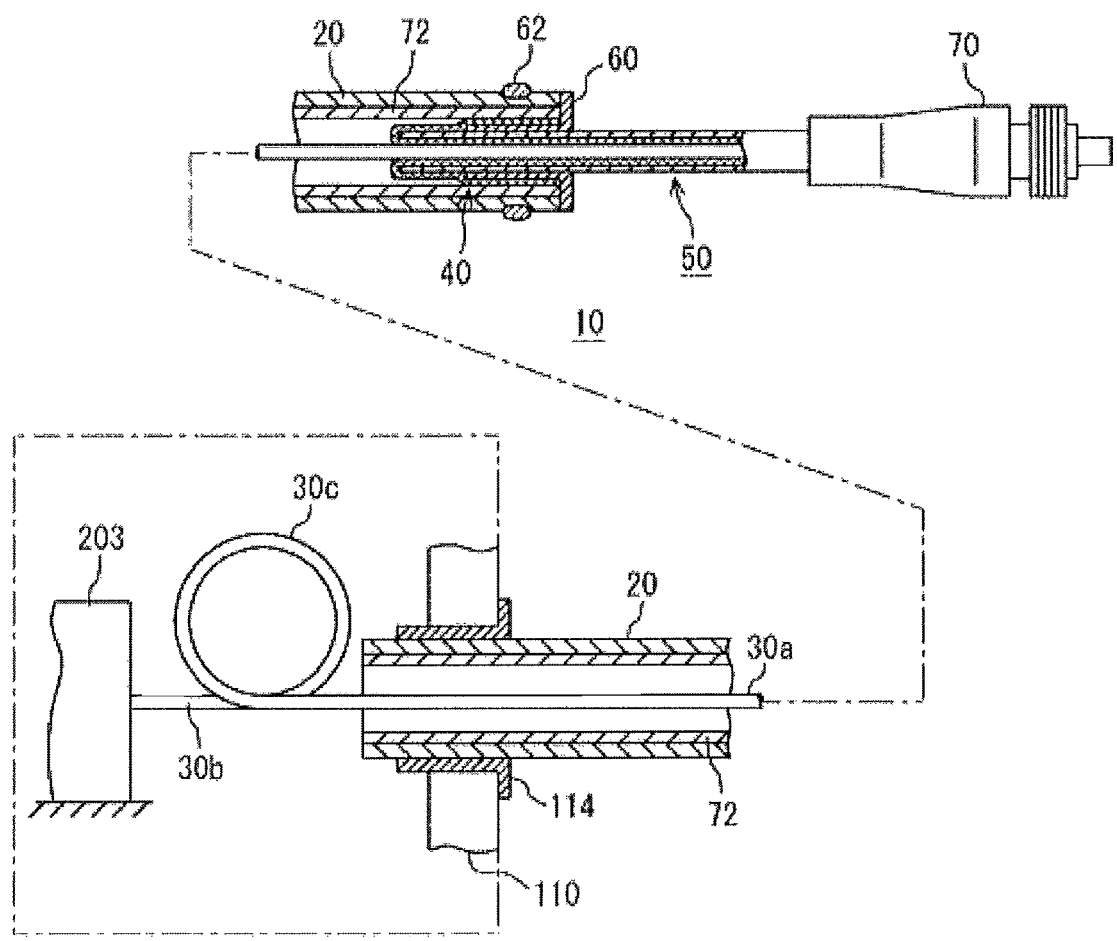
FIG. 17 is a partial longitudinal cross-sectional view showing the optical fiber of FIG. 14 applied to an optical coherence imaging diagnostic apparatus.

FIG. 17 is a cross-sectional view showing one example of using the optical cable 210 shown in FIG. 14 as a signal line for the optical coherence imaging diagnostic apparatus 100. It is clear from a comparison of FIGS. 13 and 17, the construction of the FIG. 17 example is the same as that in the FIG. 13 example, except that the former includes the resin tube 72. In view of this similarity, a detail discussion of features already discussed above in connection with the FIG. 13 embodiment will not be repeated. As shown in FIG. 17, the optical cable 210 is constructed so that the ends of the resin tube 72 are coextensive with (i.e., aligned with) the ends of the sheath. Also, the left end portion of the resin tube 72 and the left end portion of the sheath 20 are fixed to the frame portion 110 of the scanner & pullback unit 102 which functions as an optical connector.

Figure 18:
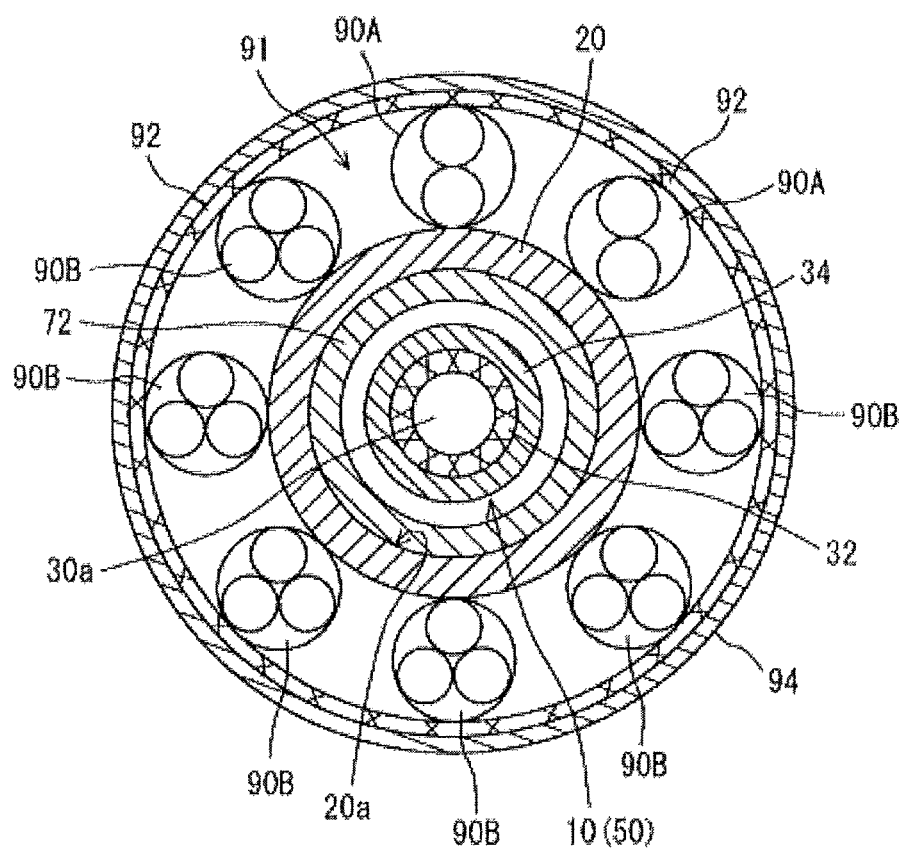
FIG. 18 is a cross-sectional view of one example of a compound optical cable.

FIG. 18 shows a case in which for the optical cable 10F, a compound optical cable is used as the signal line of the optical coherence imaging diagnostic apparatus 100. As mentioned above, with respect to the optical coherence imaging diagnostic apparatus 100, in a case in which biological tissue images are to be obtained while executing radial scan for the catheter device 101, the driving shaft 105 or the like in the catheter device 101 must be driven in a rotating manner. Therefore, in that case, a compound optical cable is used as the optical cable 10F, and this is accomplished by integrating a power line, a control signal line and the like.

FIG. 18 shows, in cross-section, an embodiment of the compound optical cable 10F. The cross-sectional view is taken at a location along the longitudinal extent of the cable at which the filling member 40 is not present. The optical cable 10F includes a plurality of electric cables 90A and signal cables 90B for this optical cable. The electric cables 90A and signal cables 90B are arranged on the radially outside of the outer circumference of the sheath 20. In this optical cable 10F, any one of the optical cables discussed above and having the constructions illustrated in FIGS. 1-17 can be used. In this illustrated embodiment, the compound optical cable 10F includes the optical cable 10' described above including the tensile strength type optical fiber 50 and the resin tube 72.

A plurality of cables 90A, 90B are positioned in the space or gap between the optical cable 10' and a protection tube 94 composed of a resin and serving as the outermost tube covering the cables 90A, 90B and the optical cable. The cables 90A, 90B include electric cables for transmitting electric power or control signals which are provided for, for example, driving the motor as mentioned above. The cables 90A, 90B are embedded in a member 91 functioning as a member for fixing and isolating the cables 90A, 90B. The fixing and isolating member 91 is a tensile strength fiber 91 in this example. In addition, a knitted line 92 for shielding is positioned between the outer circumferential surface of the tensile strength fiber 91 and the protection tube 94 in which the compound optical cable 10F is constituted.

Figure 19:
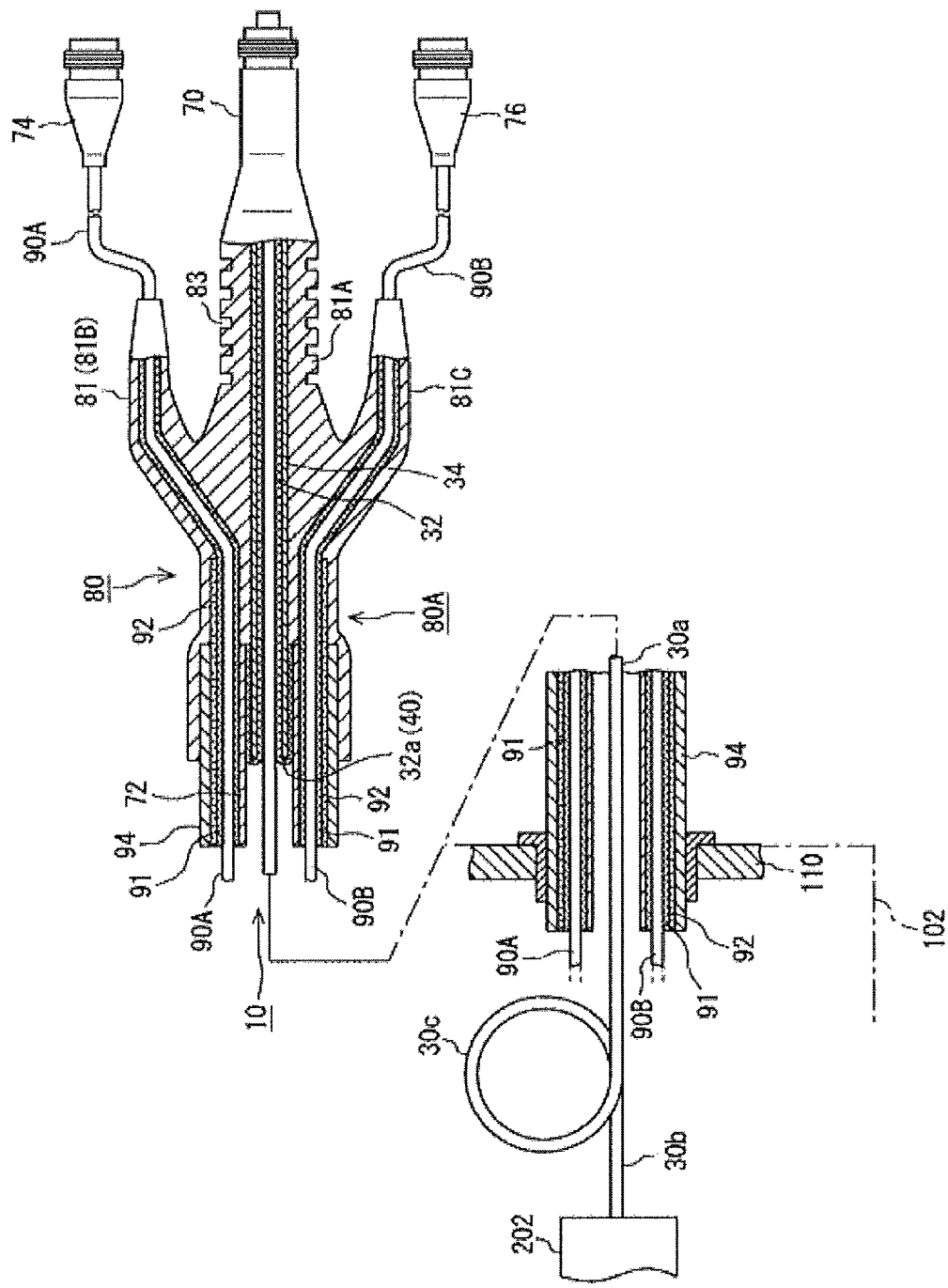
FIG. 19 is a longitudinal cross-sectional view of a portion of one example of a connector connection used together with the compound optical cable shown in FIG. 18.
Figure 20:
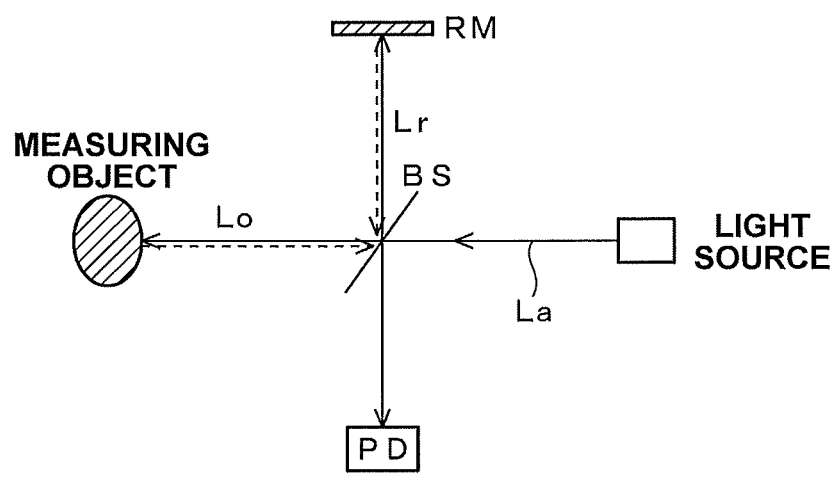
FIG. 20 is a diagram used for explaining an imaging diagnostic example in which optical coherence is used.

FIG. 19 illustrates an example of a way of using the compound optical cable 10F constructed in this manner as a signal line of the optical coherence imaging diagnostic apparatus 100 mentioned above. Assuming the right end side of the compound optical cable 10F is the optical connector 70 side, a cable branch portion 80 is provided on that right end side. The cable branch portion 80 is a molded body for mounting and fixing the compound optical cable 10F and includes a branch main body portion 80A and a plurality of limb portions (branched limb portions) 81.

The branch main body portion 80A is constructed as an aperture portion for inserting and fixing the right end portion of the compound optical cable 10F. Consequently, the optical cable 310 provided at a core portion of the compound optical cable 10F is positioned and attached on the aperture portion side in a state in which the optical fiber 50 penetrates to the branched limb portion 81 side.

In the branch main body portion 80A, the optical fiber main body 30a is fixed in the protection tube 34 by the filling member 40. The fixed region of the optical fiber main body 30a is the region from the branch main body portion 80A to the optical connector 70 or only the region of the branch main body portion 80A, and the region other than that region includes the air gap so that the optical fiber 50 is constructed in a way making it difficult to receive impacts from the outside.

The branched limb portion 81 is branched into a plurality of portions. In this example, the branched limb portion 81 includes three branches or branched portions, one for the optical cable, one for the electric cable and the third branch for the signal cable. In addition, a center limb portion 81A positioned at the center is used for the optical cable and therefore, it protrudes only by a predetermined amount of length and is configured such that the optical connector 70 is directly connected to this protruded portion 83 having a bellows construction.

Within the branched limb portions 81 positioned on both the sides of the center limb portion 81A, in this example, a limb portion 81B positioned on the upper side is used as a derivation limb portion for deriving the electric cable 90A.

It is also possible for the derivation limb portion 81B to be configured as a bundling of the plurality of electric cables 90A or to be configured so that every electric cable 90A constitutes a separate limb portion. This illustrated embodiment shows the derivation limb portion includes a plurality of bundled electric cables 90A, and the electric cables 90A extending out beyond, by predetermined lengths, from the derivation limb portion 81B are connected to a one piece connector 74.

Similarly, a limb portion 81C located on the lower side is used as a derivation limb portion for deriving the signal cable 90B which handles particularly a control signal system as an electric cable. It is also possible for the derivation limb portion 81C to be configured to bundle the plurality of signal cables 90B or also to be configured with a separate limb portion for each signal cable 90B. This illustrated embodiment shows the derivation limb portion includes a plurality of bundled signal cables 90B, and the signal cables 90B extending out beyond, by predetermined lengths, from the derivation limb portion 81C are connected to a one piece connector 76.

The three-pronged fork shaped cable branch portion 80 forming the illustrated construction and the end portion of the compound optical cable 10F are integrated by molding. Thus, the optical fiber 50, the electric cables 90A and the signal cables 90B respectively extend outwardly by predetermined amounts of lengths from the end portion of the compound optical cable 10F and among them, at least the optical connector 70 is mold-formed by an isolating resin in a state of being connected to the optical fiber 50 beforehand.

As shown in FIG. 19, the left end side of the compound optical cable 10F is fixed and passes through the frame portion 110 of the scanner & pullback unit 102. Also in this case, the outer circumference of the optical fiber main bodies 30a on the frame portion 110 side is connected to the scanner & pullback unit 102 in a state of being opened, wherein a space exists between the optical fiber main bodies 30a and the sheath 20. In addition, it is also possible, depending on the utilization mode, to separate the electric cable 90A and the signal cable 90B on the front side of the scanner & pullback unit 102.

The optical cable and optical coherence imaging diagnostic apparatus outfitted with the optical cable is well suited to avoid, preferably preventing, influences caused by external stress from being applied to or adversely impacting the inserted and attached optical fiber main body.

This optical cable disclosed here can be used for external connection such as for an optical coherence imaging diagnostic apparatus (OCT, OFDI) and the like.

The detailed description above describes preferred embodiments of the optical cable and optical coherence imaging diagnostic apparatus embodying the optical cable. However it is to be understood that the invention is not limited to those precise embodiments described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. An optical coherence imaging diagnostic apparatus comprising:
    a scanner and pullback unit connectable to an optical component, the scanner and pullback unit including a linear drive motor which linearly drives the optical component and a radial scan motor which radially scans the optical component;
    an optical connector for external input and output which inputs and outputs sample light and a reference light which are produced in an optical coherence imaging diagnostic apparatus main body and which are used for optical coherence; and
    an optical cable connected to the scanner and pullback unit and positioned between the optical connector and the scanner and pullback unit to transmit the sample light from the optical connector for external input and output and to concurrently transmit and introduce reflected light to the optical connector for external input and output;
    the optical cable having a longitudinal extent from one end to an opposite end and comprising:
        a sheath having a lumen and an inner surface;
        an optical fiber passing through the lumen in the sheath and possessing an outer surface, the optical fiber being positioned in the lumen of the sheath so that a space exists between an outer surface of the optical fiber and an inner surface of the sheath;

a filling member positioned in the space, surrounding a surrounded portion of the optical cable, and completely filling the space over a first portion of the longitudinal extent of the optical cable to fix in place the surrounded portion of the optical fiber; and a second portion of the space being devoid of the filling member.

2. The optical coherence imaging diagnostic apparatus according to claim 1, wherein the optical cable includes a surplus portion positioned between the optical fiber and the scanner and pullback unit for absorbing external stress.

3. The optical coherence imaging diagnostic apparatus according to claim 1, wherein the optical fiber is an optical fiber providing tensile strength, comprised of an optical fiber main body covered by fiber providing tensile strength.

4. The optical coherence imaging diagnostic apparatus according to claim 3, wherein the fiber providing tensile strength is the filling member.

5. The optical coherence imaging diagnostic apparatus according to claim 3, wherein the optical fiber includes a tube covering a portion of the fiber providing tensile strength which covers the optical fiber main body, a free end portion of the fiber providing tensile strength being turned back and covering an outer surface of the tube, the free end portion of the fiber providing tensile strength which is turned back forming the filling member.

6. The optical coherence imaging diagnostic apparatus according to claim 1, wherein the optical cable is a compound optical cable in which an optical fiber and an electric cable are integrated together, the compound optical cable including a cable branch portion for separating and branching the optical fiber and the electric cable.

7. The optical coherence imaging diagnostic apparatus according to claim 6, wherein the filling member completely fills the space from the cable branch portion to the optical connector, portions of the space which are not completely filled being devoid of the filling member.

8. An optical cable configured to receive sample light from a light source and to be connected to a scanner and pullback unit positioned downstream of the optical cable to transmit the light from the light source toward the scanner and pullback unit, comprising:

a sheath possessing a lumen and an inner surface;

an optical fiber located in the lumen of the sheath and possessing an outer surface, the optical fiber being configured to receive and transmit the sample light from the light source;

the lumen and the optical fiber being configured so that the inner surface of the sheath is spaced from the outer surface of the optical fiber over an entire longitudinal extent of the optical fiber;

a filling member completely filling between the inner surface of the sheath and the outer surface of the optical fiber over less than the entire longitudinal extent of the optical fiber to fix in position the optical fiber; and an air gap between the inner surface of the sheath and the outer surface of the optical fiber allowing the optical fiber to move relative to the sheath, the air gap extending over a part of the longitudinal extent of the optical fiber devoid of the filling member.

9. The optical cable according to claim 8, wherein the sheath is flexible.

10. The optical cable according to claim 8, wherein the optical fiber is an optical fiber providing tensile strength comprised of an optical fiber main body and a fiber providing tensile strength covering the optical fiber main body, the optical fiber main body including at least a core, a clad and a protection tube.

11. The optical cable according to claim 10, wherein the fiber providing tensile strength is the filling member.

12. The optical cable according to claim 8, wherein the optical cable is connected to an optical connector on a side of the optical cable at which the filling member is located.

13. The optical cable according to claim 8, wherein the optical cable is a compound optical cable in which an optical fiber and an electric cable are integrated together, the compound optical cable including a cable branch portion for separating and branching the optical fiber and the electric cable.

14. The optical cable according to claim 8, wherein the filling member completely fills between the inner surface of the sheath and the outer surface of the optical fiber from the cable branch portion to the optical connector.

* * * * *